US010555871B2

(12) United States Patent
Klimek

(10) Patent No.: US 10,555,871 B2
(45) Date of Patent: Feb. 11, 2020

(54) DEVICES AND METHODS FOR NEEDLELESS EXTRACTION AND ADMINISTRATION OF CONTENTS FROM VIALS

(71) Applicant: KLIM-LOC, LLC, Carbondale, CO (US)

(72) Inventor: Robbie Klimek, Carbondale, CO (US)

(73) Assignee: KLIM-LOC, LLC, Carbondale, CO (US)

(*) Notice: Subject to any disclaimer, the term of this patent is extended or adjusted under 35 U.S.C. 154(b) by 0 days.

(21) Appl. No.: 16/522,172

(22) Filed: Jul. 25, 2019

(65) Prior Publication Data

US 2019/0343723 A1 Nov. 14, 2019

Related U.S. Application Data

(63) Continuation of application No. PCT/US2018/033085, filed on May 17, 2018.
(Continued)

(51) Int. Cl.
*A61J 1/20* (2006.01)
*A61J 1/14* (2006.01)
(Continued)

(52) U.S. Cl.
CPC ............ *A61J 1/2051* (2015.05); *A61J 1/1481* (2015.05); *A61J 1/2096* (2013.01); *A61M 5/1782* (2013.01); *A61M 2005/3104* (2013.01)

(58) Field of Classification Search
CPC ...... A61J 1/2051; A61J 1/1481; A61J 1/2096; A61M 5/1782; A61M 2005/3104
See application file for complete search history.

(56) References Cited

U.S. PATENT DOCUMENTS 4,493,348 A * 1/1985 Lemmons ............ A61J 1/2096
138/109
4,662,878 A 5/1987 Lindmayer
(Continued)

FOREIGN PATENT DOCUMENTS

| JP | 2005-102782 | 4/2005 |
|----|-------------|--------|
| WO | WO 94/03373 | 2/1994 |
| WO | WO 2013/096911 | 6/2013 |

OTHER PUBLICATIONS

"Drug Reconstitution: Market Needs and Technical Challenges," Controlled Environments, 2011, 5 pages [retrieved online from: www.cemag.us/article/drug-reconstitution-market-needs-and-technical-challenges?page=0,1].
(Continued)

*Primary Examiner* — Andrew M Gilbert
(74) *Attorney, Agent, or Firm* — Sheridan Ross P.C.

(57) ABSTRACT

A cap assembly includes an access member including a first section and a second section. The first section includes a connection portion that is attachable to an extraction device that extracts contents of a reservoir. The connection portion includes a first opening. The second section includes a second opening in fluid communication with the contents of the reservoir when the access member is secured to the reservoir. The cap assembly includes a valve member insertable into the access member so as to be in fluid communication with the first opening and the second opening and such that the valve member i) seals the contents of the reservoir at the first opening when the connection portion is not attached the extraction device, and ii) provides access to the contents of the reservoir through the first opening when the connection portion is attached to the extraction device.

20 Claims, 10 Drawing Sheets

Related U.S. Application Data

(60) Provisional application No. 62/507,575, filed on May 17, 2017.

(51) Int. Cl.
 *A61M 5/178* (2006.01)
 *A61M 5/31* (2006.01)

(56) References Cited

U.S. PATENT DOCUMENTS

| | | | |
|---|---|---|---|
| 5,036,992 A | 8/1991 | Mouchawar et al. | |
| 5,509,433 A * | 4/1996 | Paradis | A61J 1/18 137/1 |
| 5,569,191 A | 10/1996 | Meyer | |
| 5,573,525 A | 11/1996 | Watson et al. | |
| 5,620,434 A | 4/1997 | Brony | |
| 5,833,213 A | 11/1998 | Ryan | |
| 5,971,181 A * | 10/1999 | Niedospial, Jr. | A61J 1/2096 215/247 |
| 6,056,135 A | 5/2000 | Widman | |
| 6,168,037 B1 * | 1/2001 | Grimard | A61J 1/2096 215/249 |
| 6,568,439 B1 * | 5/2003 | Se | A61J 1/2096 141/301 |
| 6,626,309 B1 | 9/2003 | Jansen et al. | |
| 6,635,043 B2 | 10/2003 | Daubert et al. | |
| 6,692,478 B1 * | 2/2004 | Paradis | A61J 1/1406 604/249 |
| 6,752,965 B2 * | 6/2004 | Levy | B01L 3/50825 215/247 |
| 7,905,873 B2 | 3/2011 | Rondeau et al. | |
| 2002/0115980 A1 * | 8/2002 | Niedospial, Jr. | A61J 1/2096 604/411 |
| 2004/0186457 A1 * | 9/2004 | Truitt | A61J 1/2096 604/403 |
| 2005/0159724 A1 * | 7/2005 | Enerson | A61J 1/2096 604/411 |
| 2008/0009822 A1 * | 1/2008 | Enerson | A61J 1/2096 604/411 |
| 2010/0241088 A1 | 9/2010 | Ranalletta et al. | |
| 2012/0104054 A1 * | 5/2012 | Terwilliger | A61J 1/1437 222/563 |
| 2012/0265163 A1 * | 10/2012 | Cheng | A61J 1/2096 604/415 |
| 2018/0168929 A1 * | 6/2018 | Stone | A61J 1/1481 |

OTHER PUBLICATIONS

"Needleless Transfer Device," West Pharmaceutical Services, Inc., 2010, 1 page [retrieved online from: www.westpharma.com/SiteCollectionDocuments/Recon/ntd instruction sheet.pdf].

"Oncology Preparation and Delivery System," Victus, 2010, 2 pages [retrieved online from: www.victus.com/products/connector-biosecurity/medical-connector-biosecurity.html].

International Search Report and Written Opinion for International (PCT) Patent Application No. PCT/US2018/033085, dated Jul. 31, 2018 12 pages.

* cited by examiner

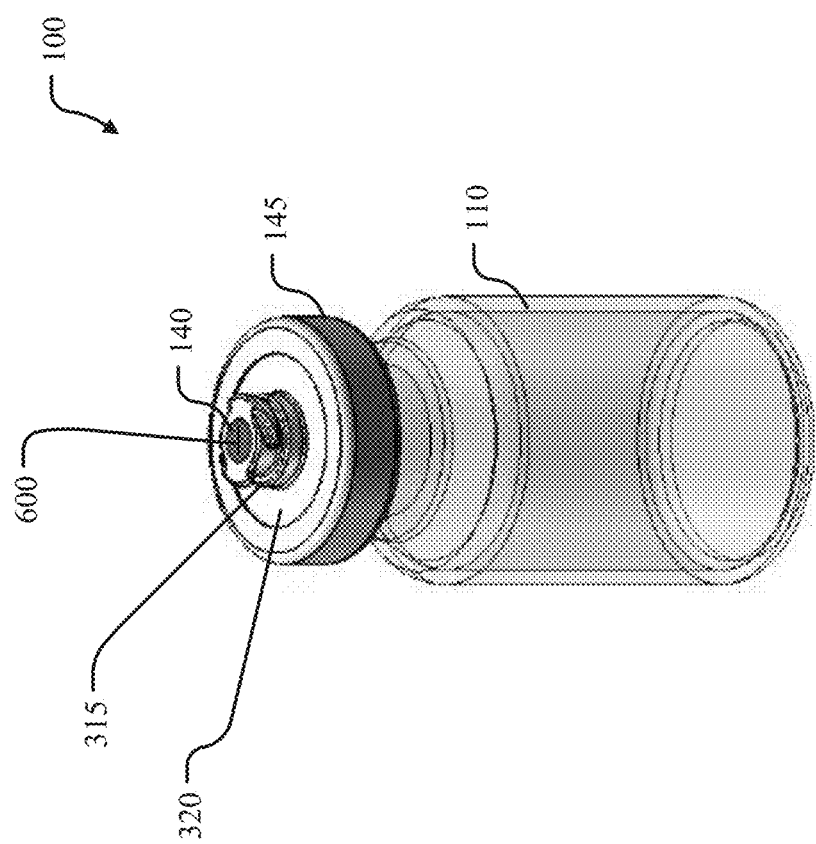

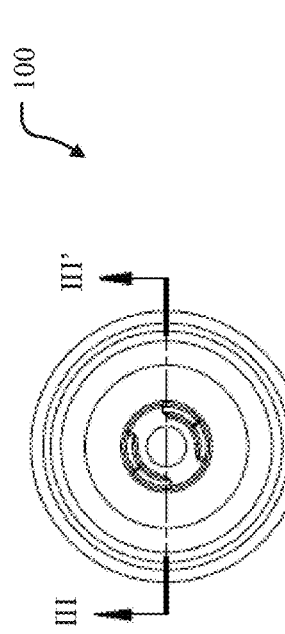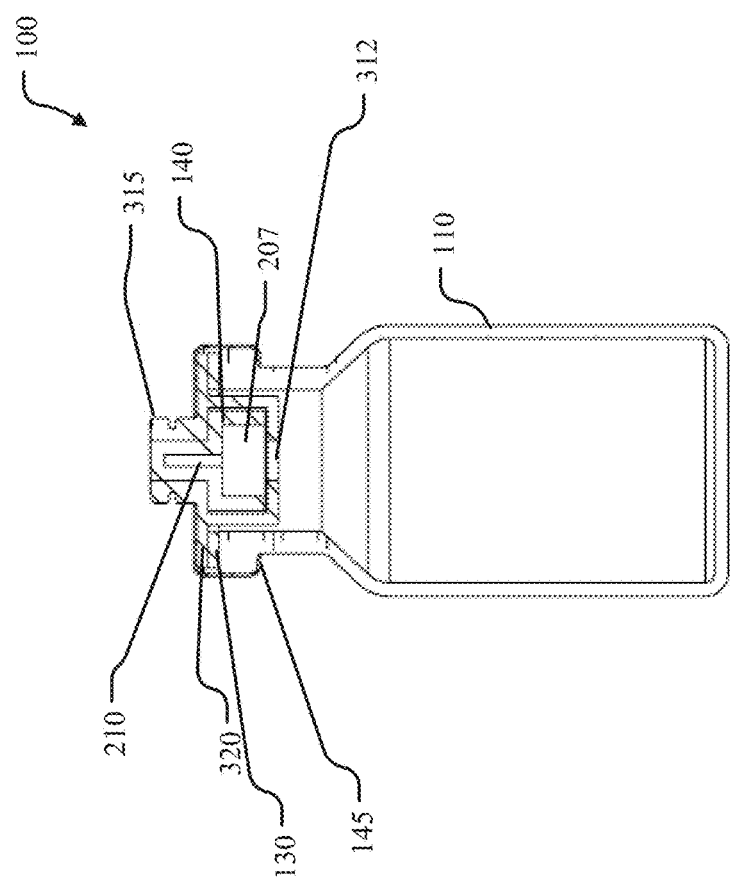

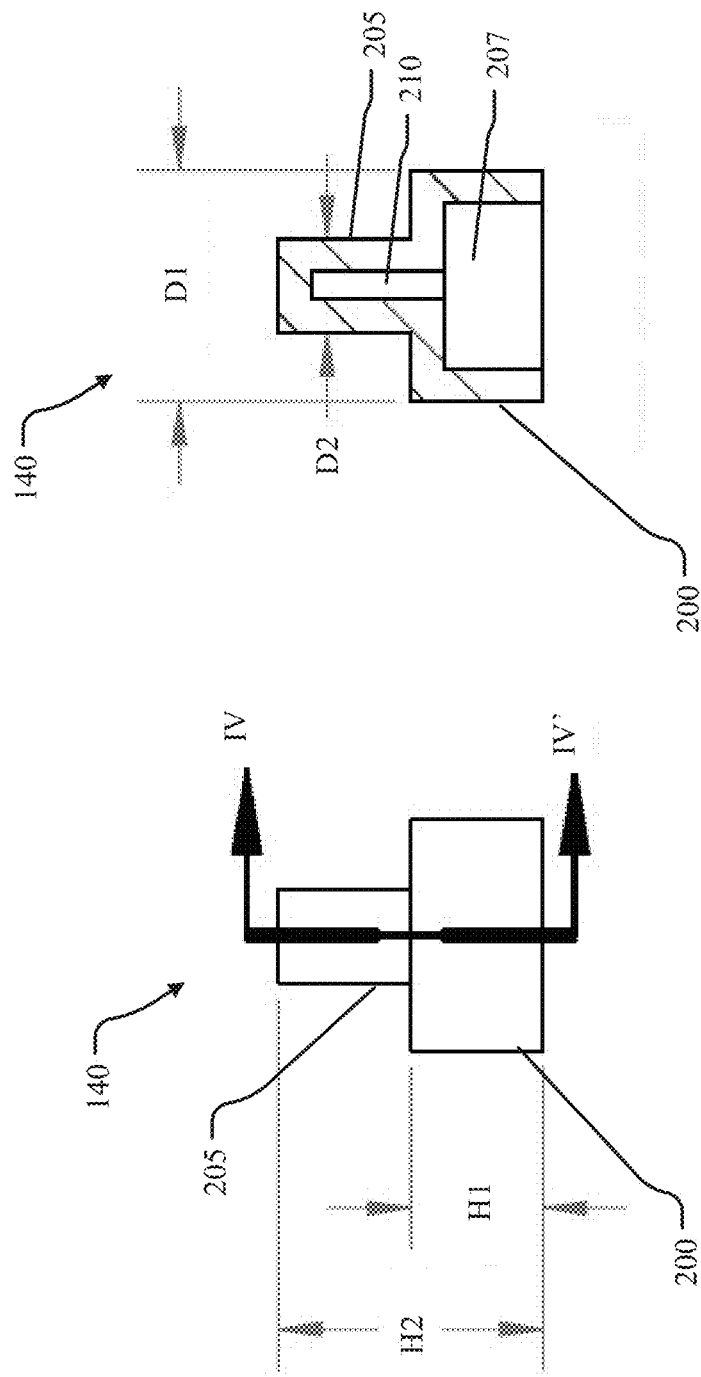

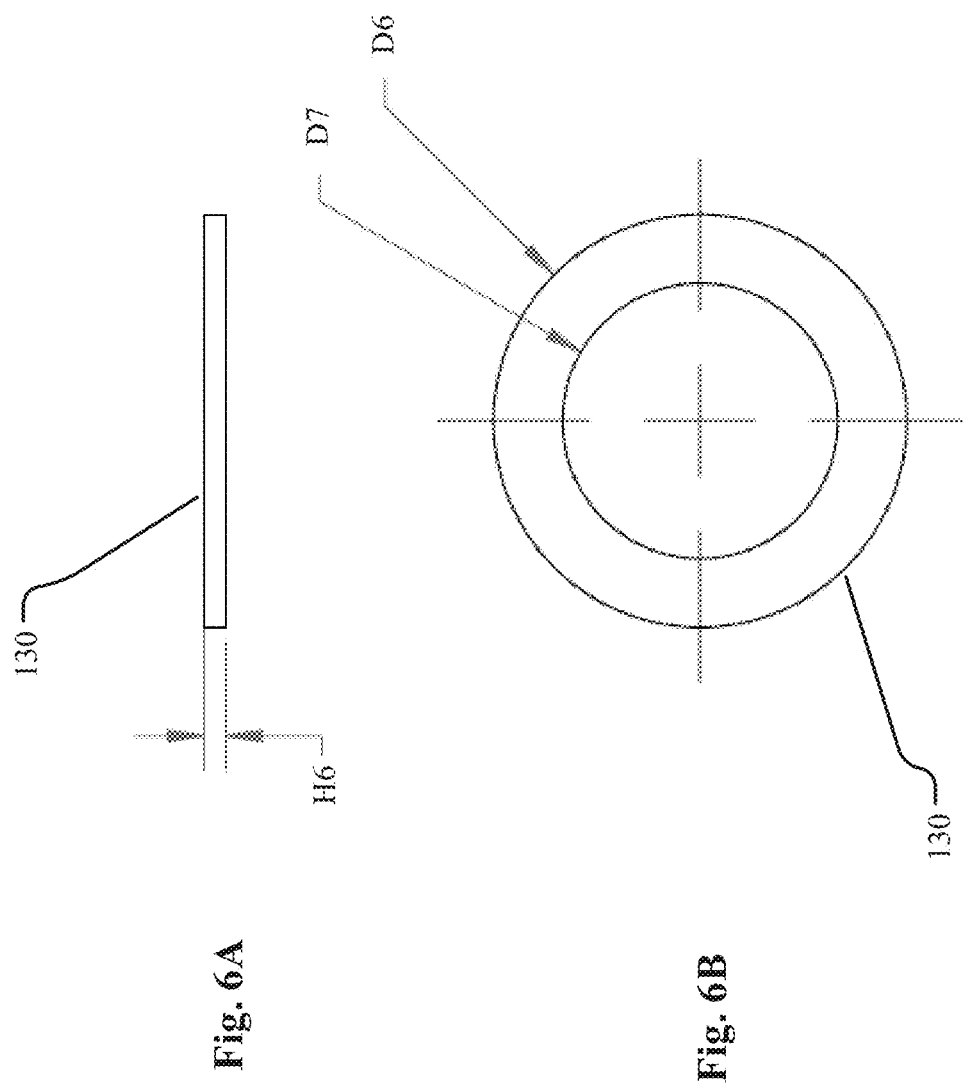

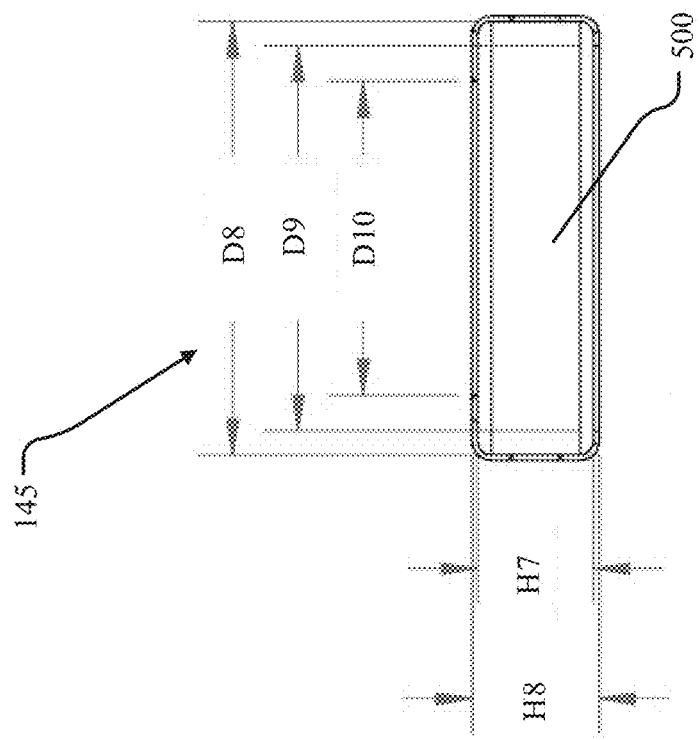
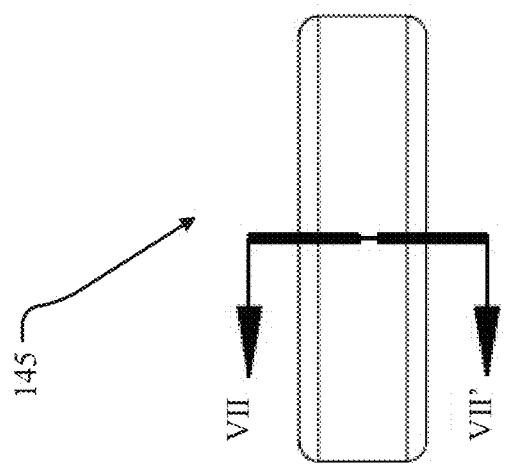
Fig. 7B
Fig. 7A

DEVICES AND METHODS FOR NEEDLELESS EXTRACTION AND ADMINISTRATION OF CONTENTS FROM VIALS

CROSS REFERENCE TO RELATED APPLICATIONS

This application is a continuation application of International Application No. PCT/US2018/033085 filed on May 17, 2018, which claims the benefit of U.S. Provisional Patent Application No. 62/507,575, filed on May 17, 2017, the entire contents of each of which are hereby incorporated by reference.

FIELD

Example embodiments generally relate to devices and/or methods for needless extraction and/or administration of contents from/to medical vials.

BACKGROUND

In the medical field, liquid is drawn from a vial or other container using a syringe and needle assembly where the needle is manually affixed the syringe and plunged into a penetrable cap of a vial to allow for extraction of the liquid from the vial into the syringe. Following extraction, the syringe/needle assembly may be administered to a patient either directly (e.g., where the needle penetrates the skin of the patient) or intravenously by plunging the needle into some type of chamber on a drip. However, the assembly of the syringe/needle is time consuming, and the extraction/administration process is subject to risks associated with handling unprotected needles (e.g., unintentional needle punctures to people or surrounding objects).

BRIEF DESCRIPTION OF THE DRAWINGS

FIG. 2 illustrates an assembled perspective view of the vial assembly of FIG. 1 according to at least one example embodiment;

FIG. 3A illustrates an assembled top view of the vial assembly in FIG. 1 according to at least one example embodiment;

FIG. 3B illustrates a cross-sectional view of the vial assembly in FIG. 3A along the line according to at least one example embodiment;

FIG. 4A illustrates side view of a valve member of the vial assembly in FIG. 1 according to at least one example embodiment;

FIG. 4B illustrates a cross-sectional view of the valve member in FIG. 4A along the line IV-IV' according to at least one example embodiment;

FIG. 6A illustrates a side view of a sealing member of the vial assembly in FIG. 1 according to at least one example embodiment;

FIG. 6B illustrates a top view of the sealing member in FIG. 6A according to at least one example embodiment;

FIG. 7A illustrates a side view of a housing of the vial assembly in FIG. 1 according to at least one example embodiment;

FIG. 7B illustrates a cross-section view of the housing in FIG. 7A along the line VII-VII' according to at least one example embodiment;

DETAILED DESCRIPTION

Figure 1:
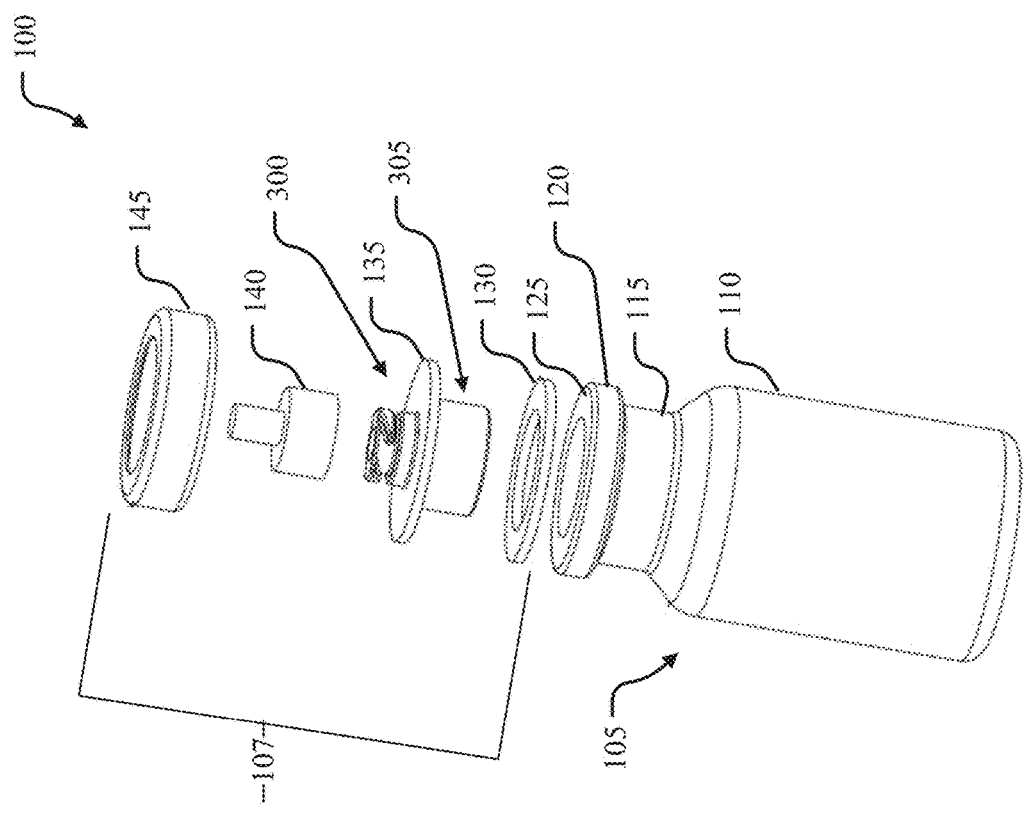
FIG. 1 illustrates an exploded view of a vial assembly according to at least one example embodiment.

Example embodiments include a vial assembly including a vial and a cap assembly that can eliminate the need for using a needle for both the extraction and administration of contents from the vial. The cap assembly includes a valve, a seal or sealing member, an access member, and a hollow housing. The valve and the sealing member may be comprised of a flexible sealing material, such as silicone. The access member may be comprised of a polymer or other plastic-type material and serves as an access port between the valve and the vial. The hollow housing may be comprised of aluminum (e.g., as an aluminum crimp) or other bendable metal that fastens the valve, the seal, and the access member to the vial.

The valve may be a hollow, unitary member that includes two integrated cylindrical portions (top and bottom) that appear concentric from a top view. The valve includes a slit in a top surface that allows liquid to flow through the valve and into the syringe. The valve may be comprised of silicone or another flexible material, such as rubber.

The access member includes a first (top) section and a second (bottom) section. Both sections may be substantially cylindrical from a top view. The first section includes a connection portion that protrudes from a top of the cap assembly and allows for connection to a syringe. For example, the connection portion may include a male thread engagement for connection to a corresponding female thread engagement on the syringe. The connection portion defines a cavity which, when assembled, fits the top portion of the valve so that the valve slit is visible on a surface of the valve that faces away from the vial. The second section also defines the cavity so that, when assembled, the second section fits the bottom portion of the valve. The second section includes an opening to allow for access to the liquid in the vial. The first section and the second section of the access member may be separable from one another at a separation point to allow for installation of the valve into the cavities of the first and second sections. After installation of the valve, the first and second sections may be bonded together by, for example, an adhesive (e.g., glue, an ultraviolet (UV) curable adhesive, a heat curable adhesive, etc.).

The seal or sealing member seals a space between the access member and the vial. The seal may comprise silicone or any other material capable of creating an airtight seal. The seal may be an O-ring seal. Although the seal is shown as being separate from the access member and the vial, it should be understood that the seal may be integrated with/adhered to at least one of the vial and the access member if desired.

The hollow housing may be comprised of a sheet metal, such as aluminum or other suitable material. Although the housing is shown in a crimped state with ends at each opening being bent over, it should be understood that the housing's initial state can be a cylindrical piece of sheet metal that fits over a top of the cap assembly and vial before being crimped on both ends to attach (e.g., permanently attach) the cap assembly to the vial.

The valve may be insertable into the access member so as to be housed within the access member so that the opening in the bottom section of the access member is aligned with the hollow portion of the valve to allow for extraction of liquid from the vial. For extraction, a user attaches a syringe to the male thread engagement of the access member that protrudes from the cap assembly. Here, the syringe has a corresponding female threaded engagement on an inner surface of one end of the syringe that surrounds a hollow protrusion that leads to a plunger section. The hollow protrusion and the female threaded engagement are arranged such that, when the syringe is screwed onto the cap assembly, the hollow protrusion pushes (or compresses) the valve toward the liquid in the vial, which causes the slit in the valve to expand and allow the liquid to flow from the vial through the opening in the access member, the valve, and the hollow protrusion and into the plunger section of the syringe upon pulling on the plunger of the syringe. In one example, the hollow protrusion extends beyond the female threaded engagement so that the protrusion makes the initial contact with the valve. Here, the valve is flexible enough so that the user can push the valve down with protrusion and simultaneously screw the syringe to the cap assembly.

An example syringe may include the hollow protrusion, the female thread on an inner surface and the plunger section.

For needless administration of the fluid in the syringe, an intravenous (IV) line or drip can have a port that employs the same or similar concepts as those described above with respect to the cap assembly. For example, drip may have an access port that utilizes the same technology as the valve, the access member, the seal and the housing. Alternatively, the drip (or whatever device is intended to receive the now extracted liquid) may employ an assembly that has the same or similar technology as the valve and the access member, but have a different means of sealing/securing the access member/valve to the drip.

In view of the above, it should be appreciated that example embodiments mitigate (or alternatively, eliminate) the disadvantages and risks of conventional devices that require assembly of a needle to a syringe for both extraction and administration of medicine from a vial. For example, the cap assembly according to example embodiments reduces the time required to assemble a device that can extract liquid from a vial since a needle does not have to be affixed to a separate syringe. Example embodiments also reduce (or alternatively eliminate) the risks associated with using a needle/syringe combination to extract and administer medicine to a patient.

FIG. 1 illustrates an exploded view of a vial assembly 100 according to at least one example embodiment.

As shown in FIG. 1, the vial assembly 100 includes a vial (or reservoir) 105 for holding contents (e.g., liquid contents) and a cap assembly 107 that can eliminate the need for using a needle for both the extraction and administration of contents from the vial 105. The vial 105 includes a body portion 110, a neck portion 115, and a rim portion 120 having a planar upper surface 125.

The cap assembly 107 includes a seal or sealing member 130, an access member 135, a valve or valve member 140, and a housing 145. The valve 140 and the sealing member 130 may be comprised of a flexible sealing material, such as silicone. The access member 135 may include sections 300 and 305 and be comprised of a polymer or other plastic-type material and serves as an access port between the valve 140 and the vial 105. The hollow housing 145 may be comprised of aluminum (e.g., as an aluminum crimp) or other bendable metal that is capable of being crimped. The details of each element in FIG. 1 are described in more detail below with reference to FIGS. 2-10.

Figures 5A, 5B:
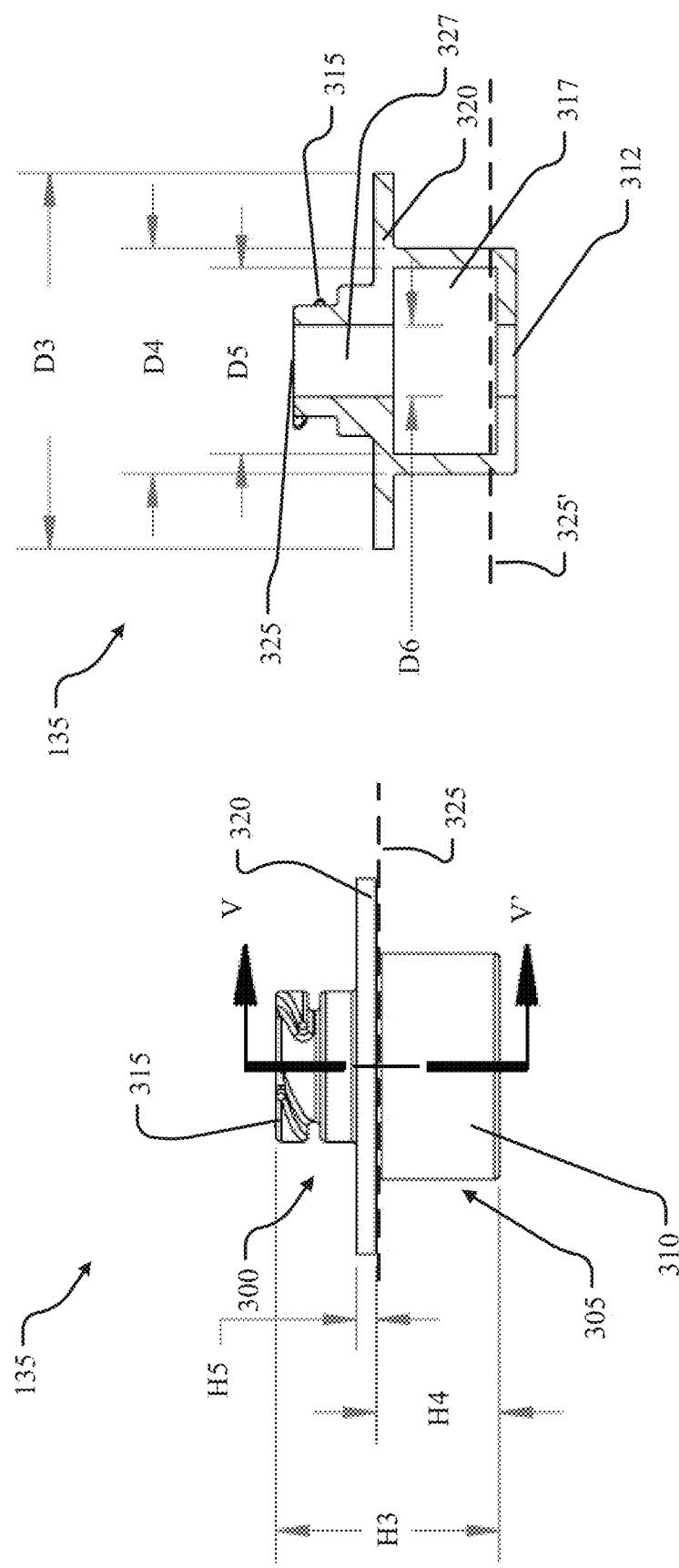
FIG. 5A illustrates a side view of an access member of the vial assembly in FIG. 1 according to at least one example embodiment.
FIG. 5B illustrates a cross-sectional view of the access member in FIG. 5A along the line V-V' according to at least one example embodiment.

FIG. 2 illustrates an assembled perspective view of the vial assembly 100 of FIG. 1 according to at least one example embodiment. FIG. 3A illustrates an assembled top view of the vial assembly 100 in FIGS. 1 and 2 according to at least one example embodiment. FIG. 3B illustrates a cross-sectional view of the vial assembly 100 in FIG. 3A along the line according to at least one example embodiment. FIG. 4A illustrates side view of a valve 140 of the vial assembly 100 in FIG. 1 according to at least one example embodiment. FIG. 4B illustrates a cross-sectional view of the valve 140 in FIG. 4A along the line IV-IV' according to at least one example embodiment. FIG. 5A illustrates a side view of an access member 135 of the vial assembly 100 in FIG. 1 according to at least one example embodiment. FIG. 5B illustrates a cross-sectional view of the access member 135 in FIG. 5A along the line V-V' according to at least one example embodiment. FIG. 6A illustrates a side view of a sealing member 130 of the vial assembly 100 in FIG. 1 according to at least one example embodiment. FIG. 6B illustrates a top view of the sealing member 130 in FIG. 6A according to at least one example embodiment. FIG. 7A illustrates a side view of a housing 145 of the vial assembly in FIG. 1 according to at least one example embodiment. FIG. 7B illustrates a cross-section view of the housing 145 in FIG. 7A along the line VII-VII' according to at least one example embodiment.

As shown in FIG. 2, by way of crimping the housing 145, the remainder of the cap assembly 107 is fixable to the vial 105. For example, the housing 145 slides over the valve 140, the sealing member 130, and the access member 135, and the rim portion 120 before being crimped around the access member 135 and the rim portion 120 to fasten the cap assembly 107 to the vial 105.

With reference to FIGS. 1-7B, the cap assembly 107 may include the access member 135 including a first section 300 and a second section 305 (see FIG. 1 and FIGS. 5A and 5B). The first section 300 includes a connection portion 315 that is attachable to an extraction device (e.g., a syringe 800 as in FIGS. 8A-9) that extracts (or inserts) contents of the reservoir 105. As shown in FIGS. 3B, 5A and 5B, the connection portion 315 includes a first opening 325, and the second section 305 includes a second opening 312 in fluid communication with the contents of the reservoir 105 when the access member 135 is secured to the reservoir 105. As also shown in FIGS. 5A and 5B, the connection portion 315 may protrude from the access member 135 and include a male connector, such as a male connector with an outer thread for a screw connection to a corresponding female connector with an inner thread (see FIGS. 8A and 8B).

As shown in FIGS. 1-3B, the valve member 140 is insertable into the access member so as to be housed within the access member so that the opening 312 in the second section 305 of the access member 135 is aligned with the hollow portions 207/210 of the valve 140 to allow for extraction of contents from the vial 105. As shown in FIG. 2, the valve member 140 may include a top portion with a slit 600, which is located in the first opening 325 of the connection portion 315 when the cap assembly 107 is fixed to the vial 105. According to at least one example embodiment, the valve member 140 is comprised of a flexible material, such as silicone, so that the valve member 140 is compressible relative to the first opening 325. Here, it should be appreciated that the slit 600, in an uncompressed state of the valve member 140, is closed and seals the contents of the reservoir 105 at the first opening 325 when the connection portion 315 is not attached to the extraction device. Additionally, the slit 600, in a compressed state of the valve member 140, opens and provides the access to the contents of the reservoir 105 when the connection portion 315 is attached the extraction device (e.g., syringe 800 in FIGS. 8A and 8B). Upon attachment of the connection portion 315 to the extraction device, contents of the reservoir 105 are ready to be extracted. In other words, the valve member 140 is insertable into the access member 135 so as to be housed in the access member 135 and in fluid communication with the first opening 325 and the second opening 315 and such that the valve member 140 i) seals the contents of the reservoir 105 at the first opening 325 when the connection portion 315 is not attached the extraction device (e.g., syringe 800 in FIG. 9), and ii) provides access to the contents of the reservoir 105 through the first opening 325 when the connection portion 315 is attached to the extraction device.

As shown in FIGS. 4A and 4B, the valve member 140 may have a first section 200 and a second section 205. The first section 200 and the second section 205 are substantially cylindrical shaped. The first section 200 includes a first hollow portion 207 and the second section 205 includes a second hollow portion 210. As shown in FIGS. 3A and 3B, the hollow portions 207/210 are in fluid communication with the reservoir 105 through the opening 312 in the access member 135. In addition, the hollow portion 210 is fluid communication with the slit 600 in FIG. 2 to allow for extraction of the contents from the reservoir 105. The first section 200 may have a height H1 of about 0.200 in, and a diameter D1 of about 0.350 in. The first and second sections 200 and 205 may have a total height H2 of about 0.400 in. The second section 205 may have a diameter D2 of about 0.143 in.

As shown in FIGS. 5A and 5B, the access member 135 includes the first section 300 and the second section 305. In order to allow the valve member 140 to be inserted into the access member 135 (as shown in FIGS. 2 and 3B), the access member 135 may be physically cut into the first section 300 and the second section 305, for example, along the line 325. Alternatively, sections 300 and 305 are manufactured as separate pieces. In any event, after the valve member 140 is inserted into the one of the sections 300/305, the sections 300 and 305 are adhered to one another, for example, by ultraviolet (UV) curing, heat curing, or other suitable adhesive technique. In other words, the first section 300 and the second section 305 are detachably connected. Thus, according to at least one example embodiment, the sections 300 and 305 comprise a UV or heat curable material. Although FIG. 5A shows that the sections 300 and 305 are separated along the line 325, it should be appreciated that other separation locations may be used according to design and/or manufacturing preferences. For example, FIG. 5B shows another example separation location along the line 325'. The first section 300 may include a planar portion 320 that is designed to rest on the sealing member 130 and be supported by the rim portion 125 of the vial 105. As shown in FIGS. 3B and 5B, the access member 135 includes hollow portions 317 and 327 to accommodate the valve member 140.

As shown in FIGS. 5A and 5B, the access member 135 has a total height H3 of about 0.445 in., the second section 305 has a height H4 of about 0.246 in, and the planar portion 320 has a height H5 of about 0.039 in. In addition, a diameter D3 of the access member 135 is about 0.750 in., a diameter D4 of the second section 305 is about 0.450 in., a diameter D5 of the hollow portion 317 is about 0.371 in, and a diameter D6 of the openings 312 and 325 is about 0.143 in.

As shown in FIGS. 6A and 6B, a height H6 of the sealing member 130 may be about 0.040 in., an outer diameter D6 of the sealing member 130 is about 0.750 in, and an inner diameter D7 of the sealing member 130 is about 0.500 in. With reference to FIGS. 1 and 3B, it should be appreciated that the sealing member 130 seals an interface between the reservoir 105 (e.g., the planar surface 125) and the planar portion 320 of the access member 135. The sealing member 130 may be comprised of a flexible sealing material, such as rubber, silicone, or other suitable sealing material. Although the sealing member 130 is shown as an element separate from the vial 105, it should be understood that the sealing member 130 may also be integrated with the vial 105, for example, via a pre-existing attachment to the planar surface 125 of the rim portion 120.

FIGS. 7A and 7B illustrate additional details of the housing 145. As noted above, the housing 145, secures the access member 135 and the sealing member 130 to the reservoir 105. According to at least one example embodiment, the housing 145 is a bendable and hollow cylinder with openings at each end. To secure the access member 135 and the sealing member 130 to the vial 105, the housing 145 slides over the remainder of the cap assembly 107 and the rim portion 125. Then, both ends of the housing 145 are bent (or crimped) toward a center of the housing 145 to fix the cap assembly 107 to the vial 105. According to at least one example embodiment, the housing is a metal, such as aluminum.

As shown in FIGS. 7A and 7B, a final, assembled, height H7 of the housing 145 may be about 0.211 in., while an initial, pre-assembled, height H8 of the housing 145 may be about 0.231 in. Here, the initial height H8 refers to a height of the housing prior to attachment of the cap assembly 107 to the vial 105, i.e., prior to the ends of the housing 145 being bent toward the center of the housing 145 to secure the access member 135 and the sealing member 130 to the vial as shown in FIG. 2. In addition, the final height H7 refers to a height of the housing 145 after attachment of the cap assembly 107 to the vial 105, i.e., after bending the ends of the housing 145 toward the center to secure the access member 135 and the sealing member 130 to the vial 105 as shown in FIG. 2. An outer diameter D8 of the housing 145 may be about 0.787 in., an intermediate diameter D9 of the housing 145 may be about 0.700 in., and an inner diameter D10 of the housing 145 may be about 0.570 in.

Figures 8A, 8B:
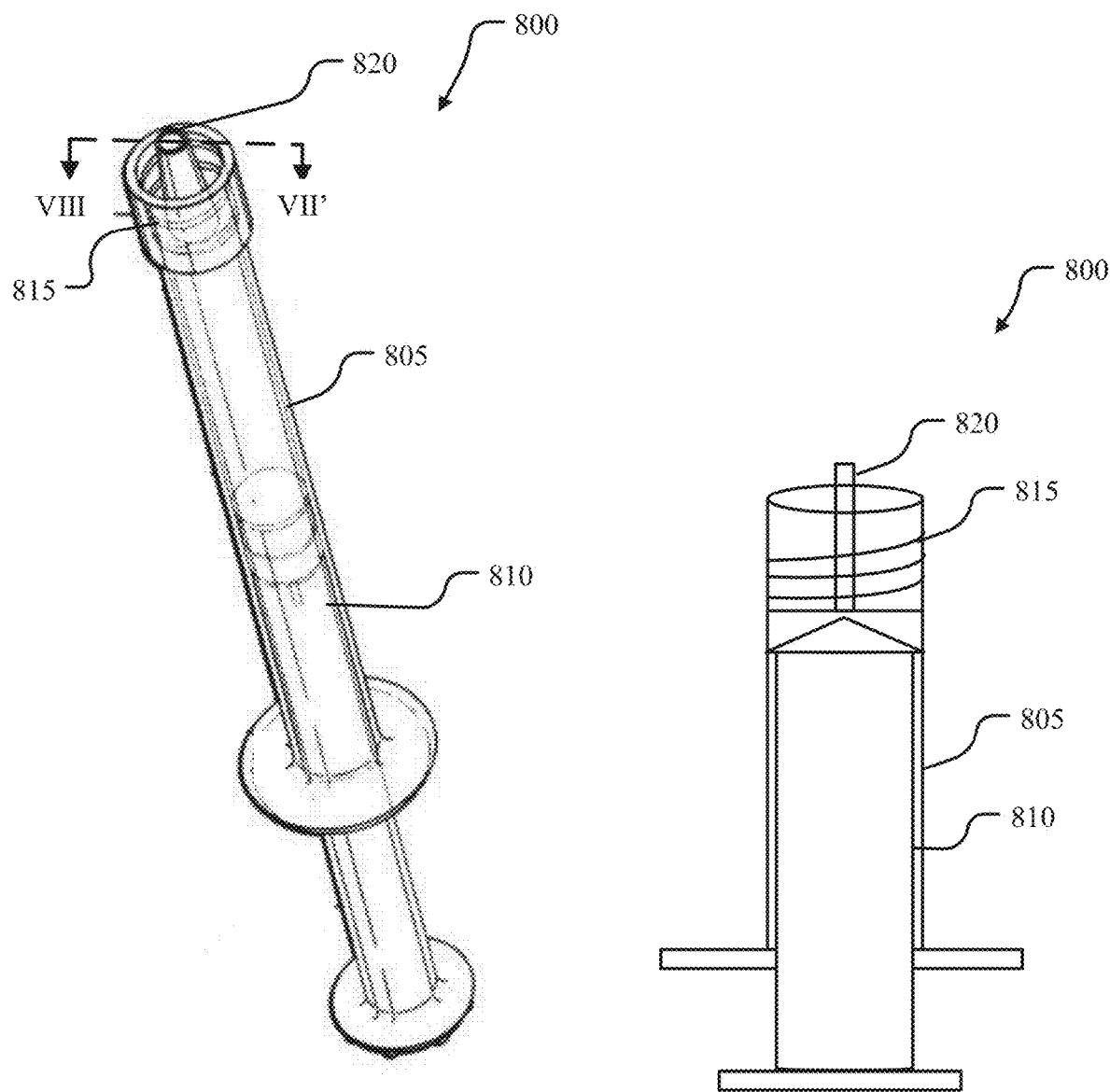
FIG. 8A illustrates a perspective view of a syringe according to at least one example embodiment.
FIG. 8B illustrates a cross-sectional view of the syringe in FIG. 8B along the line VIII-VIII' according to at least one example embodiment.

FIG. 8A illustrates a perspective view of a syringe 800 according to at least one example embodiment. FIG. 8B illustrates a cross-sectional view of the syringe 800 in FIG. 8B along the line VIII-VIII' according to at least one example embodiment.

As shown in FIGS. 8A and 8B, the syringe 800 includes a hollow holding portion 805, a plunger 810, a connection portion 815, and a tip 820. The connection portion 815 may include a female thread for engagement with the male thread of the connection portion 315. The tip 820 may protrude beyond an upper surface of the connection portion 815 in order to allow for the tip 820 to penetrate the connection portion 315 when connecting the syringe 800 to the vial assembly 100, thereby compressing the valve member 140.

Figure 9:
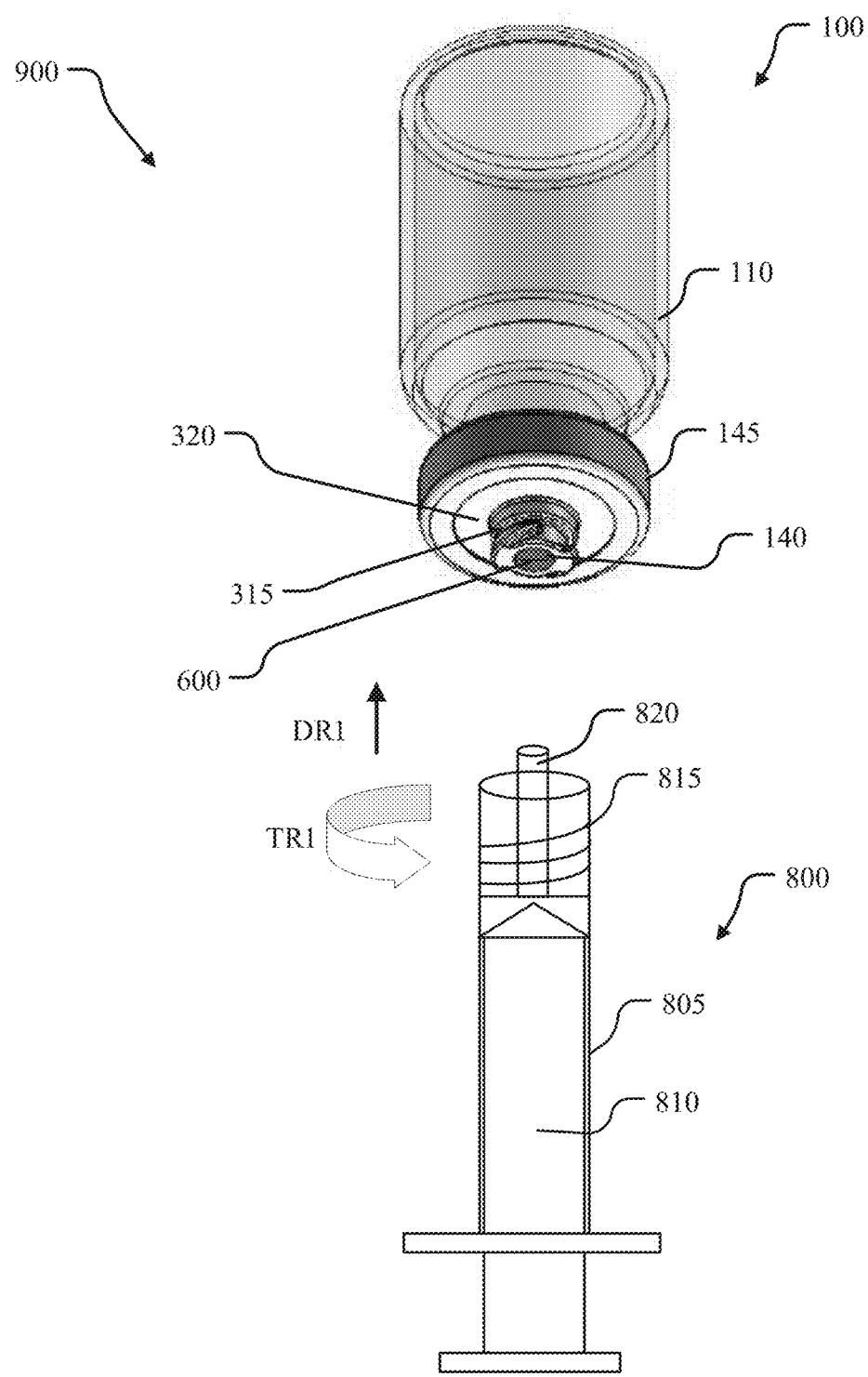
FIG. 9 illustrates a package including the syringe in FIGS. 8A and 8B and the vial assembly of FIGS. 1-7B according to at least one example embodiment.

FIG. 9 illustrates a package 900 including the syringe 800 in FIGS. 8A and 8B and the vial assembly 100 of FIGS. 1-7B according to at least one example embodiment. FIG. 9 illustrates an example of the syringe (or extraction device) 800 being moved in a direction DR1 toward the vial assembly 100 such that the tip 820 penetrates the connection portion 315 to thereby compress the valve member 140 and open the slit 600 to provide access to the contents of the vial 105. As the tip 820 compresses the valve member 140, the syringe 800 may be twisted in the clockwise direction TR1 in order to engage the female thread on the connection portion 815 with the male thread on the connection portion 315. Now, the syringe 800 and the vial assembly 100 are attached to one another in a manner that allows the contents of the vial to be extracted or inserted by, for example, actuation of the plunger 810. In order to release the syringe 800 from the vial assembly 100, the syringe 800 may be twisted in the counter-clockwise direction to disengage the female thread of the connection portion 815 from the male thread of the connection portion 315.

In view of FIGS. 1-9, it should be understood that the valve member 140 is insertable into the access member 135 so as to be housed in the access member 135 and in fluid communication with the first opening 325 and the second opening 315 such that the valve member 140 i) seals the contents of the reservoir 105 at the first opening 325 when the connection portion 315 is not attached the extraction device 800, and ii) provides access to the contents of the reservoir 105 through the first opening 325 when the connection portion 315 is attached to the extraction device 800. Here, it should be appreciated that the slit 600, in an uncompressed state of the valve member 140, seals the contents of the reservoir 105 at the first opening 325 when the connection portion 315 is not attached to the extraction device 800. Additionally, the slit 600, in a compressed state of the valve member 140, provides the access to the contents of the reservoir 105 when the connection portion 315 is attached the extraction device (e.g., syringe 800 in FIG. 9). Upon attachment of the connection portion 315 to the extraction device 800, contents of the reservoir 105 are ready to be extracted.

Figure 10:
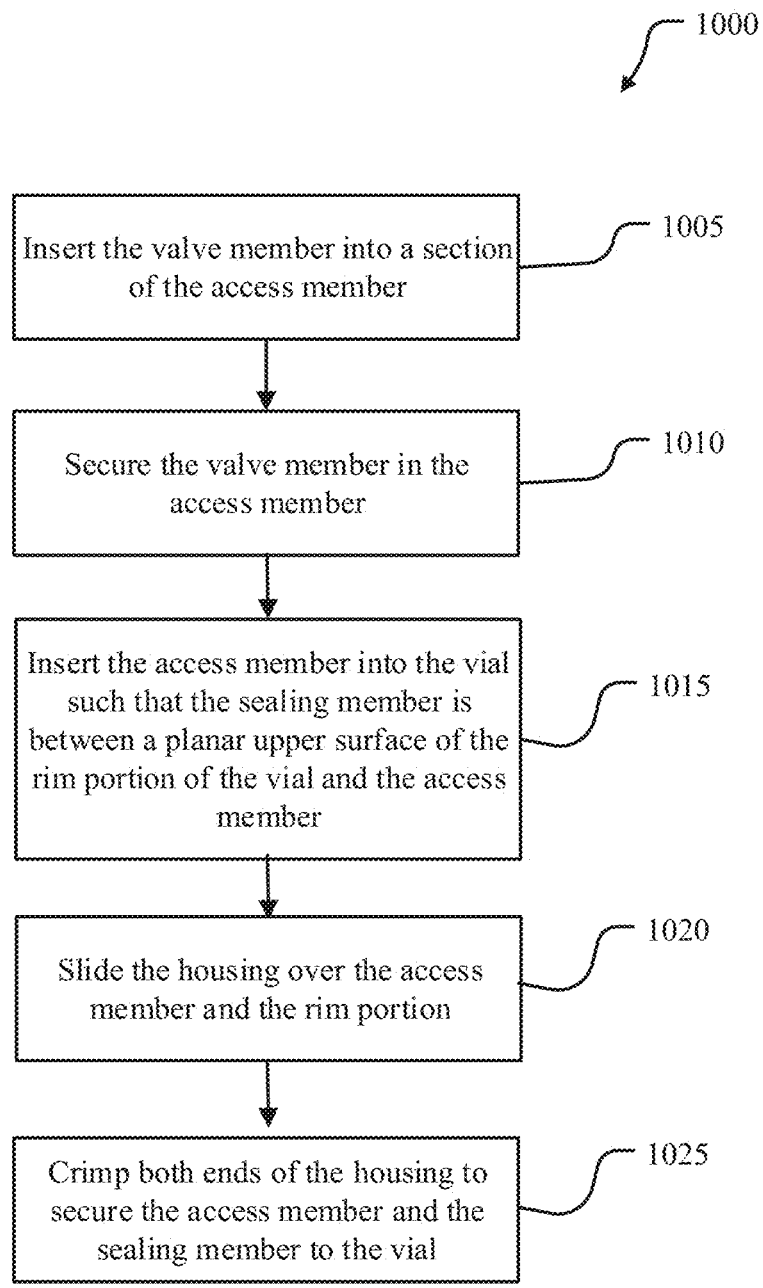
FIG. 10 illustrates a method of manufacturing the vial assembly in FIGS. 1-7B according to at least one example embodiment.

FIG. 10 illustrates a method 1000 of manufacturing the vial assembly 100 in FIGS. 1-7B according to at least one example embodiment.

While a general order for the steps of the method 1000 is shown in FIG. 10, the method 1000 can include more or fewer steps or can arrange the order of the steps differently than those shown in FIG. 10 if desired. Hereinafter, the FIG. 10 shall be explained with reference to the systems, components, assemblies, devices, user interfaces, environments, software, etc. described in conjunction with FIGS. 1-9.

In operation 1005, the method 1000 includes inserting the valve member 140 into a section of the access member 135. As noted above, the access member 135 is split into sections, for example, sections 300/305 to allow for insertion of the valve member 140.

In operation 1010, the method 1000 includes securing the valve member 140 in the access member 135, for example, by adhering section 300 to section 305 using a suitable adherent and/or adhering process.

In operation 1015, the method 1000 includes inserting the access member 135 into the vial 105 (e.g., the neck 115) such that the sealing member 130 is between the planar upper surface 125 of the rim portion 120 and the access member 135 (e.g., a bottom surface of the planar portion 320).

In operation 1020, the method 1000 includes sliding the housing 145 over the access member 135 and the rim portion 120.

In operation 1025, the method 1000 includes crimping (or bending) both ends of the housing 145 to secure the access member 135 and the sealing member 130 to the vial 105. For example, one end of the housing 145 is bent toward a central axis of the vial 105 in order to make contact with an upper surface of the planar portion 320. The other end of the housing is bent toward the central axis of the vial 105 so as to make contact with a bottom surface of the rim portion 120. Now, cap assembly (including the sealing member 130, the access member 135, the valve member 140, and the housing 145 are secured to the vial 105 to complete the vial assembly 100.

In view of the above, it should be appreciated that example embodiments mitigate (or alternatively, eliminate) the disadvantages and risks of conventional devices that involve assembly of a needle to a syringe for insertion/extraction and administration of medicine from a vial. For example, a cap assembly according to example embodiments reduces the time required to assemble a device that can extract liquid from a vial since a needle does not have to be affixed to a separate syringe. Example embodiments also reduce (or alternatively eliminate) the risks associated with using a needle/syringe combination to extract and administer medicine to a patient.

For needless administration of the fluid in the syringe, an IV line or drip can have a port that employs the same or similar concepts as those described above with respect to the cap assembly. For example, drip may have an access port that utilizes the same technology as the valve, the access member, the seal and the housing. Alternatively, the drip (or whatever device is intended to receive the now extracted liquid) may employ an assembly that has the same or similar technology as the valve and the access member, but have a different means of sealing/securing the access member/valve to the drip.

The foregoing description and figures show approximate dimensions (in inches) and example shapes and sizes of the valve, the seal, the access member, the housing, the syringe, the vial, etc. However, example embodiments are not limited to thereto, and the sizes and shapes of each element may vary according to design preferences (e.g., the size of the vial). In addition, it should be understood that example embodiments are not limited to the types of connectors (e.g., male thread, female thread) disclosed herein. For example, other suitable connections (e.g., detent connections) may be employed if desired without departing from the spirit and scope of example embodiments.

The phrases "at least one", "one or more", "or", and "and/or" are open-ended expressions that are both conjunctive and disjunctive in operation. For example, each of the expressions "at least one of A, B and C", "at least one of A, B, or C", "one or more of A, B, and C", "one or more of A, B, or C", "A, B, and/or C", and "A, B, or C" means A alone, B alone, C alone, A and B together, A and C together, B and C together, or A, B and C together.

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

Various aspects of the example embodiments are described herein with reference to drawings that are schematic illustrations of idealized configurations. It should be appreciated that while particular configurations and elements are described herein, example embodiments are not limited to the illustrative configurations and/or elements depicted and described herein. Specifically, it should be appreciated that elements of a particular type or function may be replaced with one or multiple other elements to achieve a similar function without departing from the scope of example embodiments.

The present disclosure, in various aspects, embodiments, and/or configurations, includes components, methods, processes, systems and/or apparatus substantially as depicted and described herein, including various aspects, embodiments, configurations embodiments, sub combinations, and/or subsets thereof. Those of skill in the art will understand how to make and use the disclosed aspects, embodiments, and/or configurations after understanding the present disclosure. The present disclosure, in various aspects, embodiments, and/or configurations, includes providing devices and processes in the absence of items not depicted and/or described herein or in various aspects, embodiments, and/or configurations hereof, including in the absence of such items as may have been used in previous devices or processes, e.g., for improving performance, achieving ease and\or reducing cost of implementation.

The foregoing discussion has been presented for purposes of illustration and description. The foregoing is not intended to limit the disclosure to the form or forms disclosed herein. In the foregoing Detailed Description for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as an example embodiment of the disclosure.

At least one example embodiment includes a cap assembly including an access member including a first section and a second section, the first section including a connection portion that is attachable to an extraction device that extracts contents of a reservoir, the connection portion including a first opening, the second section including a second opening in fluid communication with the contents of the reservoir when the access member is secured to the reservoir. The cap assembly includes a valve member insertable into the access member and in fluid communication with the first opening and the second opening and such that the valve member i) seals the contents of the reservoir at the first opening when the connection portion is not attached the extraction device, and ii) provides access to the contents of the reservoir through the first opening when the connection portion is attached to the extraction device.

According to at least one example embodiment, the cap assembly includes a sealing member to seal an interface between the reservoir and the access member, and a housing that secures the access member and the sealing member to the reservoir.

According to at least one example embodiment, the housing is a bendable and hollow cylinder, and wherein ends of the housing are bent toward a center of the cylinder to secure the access member and the sealing member to the reservoir.

According to at least one example embodiment, the housing is a metal.

According to at least one example embodiment, the valve member is a flexible material.

According to at least one example embodiment, the valve member is compressible and includes a top portion with a slit located in the first opening of the connection portion when the valve member is inserted into the access member.

According to at least one example embodiment, the slit, in an uncompressed state of the valve member, seals the contents of the reservoir at the first opening when the connection portion is not attached to the extraction device. The slit, in a compressed state of the valve member, provides the access to the contents of the reservoir when the connection portion is attached the extraction device.

According to at least one example embodiment, the first section and the second section are detachably connected.

According to at least one example embodiment, the connection portion protrudes from the access member and includes a male thread to engage with a female thread of the extraction device.

At least one example embodiment includes a vial assembly including a reservoir to hold contents, and a cap assembly fixable to the reservoir. The cap assembly includes an access member including a first section and a second section, the first section including a connection portion that is attachable to an extraction device that extracts the contents from the reservoir, the connection portion including a first opening, the second section including a second opening in fluid communication with the contents of the reservoir when the access member is secured to the reservoir. The cap assembly includes a valve member insertable into the access member and in fluid communication with the first opening and the second opening and such that the valve member i) seals the contents of the reservoir at the first opening when the connection portion is not attached the extraction device, and ii) provides access to the contents of the reservoir through the first opening when the connection portion is attached to the extraction device.

At least one example embodiment includes a package including a reservoir to hold contents, an extraction device to at least one of extract or insert the contents, a cap assembly fixable to the reservoir. The cap assembly includes an access member including a first section and a second section, the first section including a connection portion that is attachable to the extraction device that extracts contents of the reservoir, the connection portion including a first opening, the second section including a second opening in fluid communication with the contents of the reservoir when the access member is secured to the reservoir. The cap assembly includes a valve member insertable into the access member and in fluid communication with the first opening and the second opening and such that the valve member i) seals the contents of the reservoir at the first opening when the connection portion is not attached the extraction device, and ii) provides access to the contents of the reservoir through the first opening when the connection portion is attached to the extraction device.

What is claimed is:

1. A cap assembly, comprising:
   an access member including a first section and a second section, the first section including a connection portion that is attachable to an extraction device that extracts contents of a reservoir, the connection portion including a first opening, the second section including a second opening in fluid communication with the contents of the reservoir when the access member is secured to the reservoir;

a valve member insertable into the access member so as to be in fluid communication with the first opening and the second opening and such that the valve member i) seals the contents of the reservoir at the first opening when the connection portion is not attached the extraction device, and ii) provides access to the contents of the reservoir through the first opening when the connection portion is attached to the extraction device;

a sealing member; and a housing separate from the reservoir and configured to secure the access member and the sealing member to the reservoir such that the sealing member is between the reservoir and the access member, wherein, when the valve member is inserted into the access member, the valve member extends from the connection portion of the access member to the second opening of the access member.

2. The cap assembly of claim 1,
wherein the sealing member is ring shaped and the housing is a hollow cylinder, and
wherein an outermost diameter of the sealing member is less than an outermost diameter of the housing.

3. The cap assembly of claim 2, wherein the housing is bendable, and wherein ends of the housing are bent toward a center of the hollow cylinder to secure the access member and the sealing member to the reservoir.

4. The cap assembly of claim 3, wherein the housing includes metal.

5. The cap assembly of claim 1, wherein the valve member is a flexible material, wherein the valve member includes a first part and a second part, wherein an outermost diameter of the first part is less than an outermost diameter of the second part, and wherein, when the valve member is inserted into the access member, the first part of the valve member is located in the connection portion of the access member and the second part of the valve member is located in the second section of the access member.

6. The cap assembly of claim 5, wherein the valve member is compressible and includes a top portion with a slit located in the first opening of the connection portion when the valve member is inserted into the access member.

7. The cap assembly of claim 6, wherein the slit, in an uncompressed state of the valve member, seals the contents of the reservoir at the first opening when the connection portion is not attached to the extraction device, and wherein the slit, in a compressed state of the valve member, provides the access to the contents of the reservoir when the connection portion is attached the extraction device.

8. The cap assembly of claim 1, wherein the first section and the second section are detachably connected.

9. The cap assembly of claim 1, wherein the connection portion protrudes from a planar portion of the first section and includes a male thread to engage with a female thread of the extraction device.

10. A vial assembly, comprising:
a reservoir to hold contents; and
a cap assembly fixable to the reservoir, the cap assembly including,
an access member including a first section and a second section, the first section including a connection portion that is attachable to an extraction device that extracts the contents from the reservoir, the connection portion including a first opening, the second section including a second opening in fluid communication with the contents of the reservoir when the access member is secured to the reservoir, a valve member insertable into the access member so as to be in fluid communication with the first opening and the second opening and such that the valve member i) seals the contents of the reservoir at the first opening when the connection portion is not attached the extraction device, and ii) provides access to the contents of the reservoir through the first opening when the connection portion is attached to the extraction device, a sealing member, and a housing separate from the reservoir and configured to secure the access member and the sealing member to the reservoir such that the sealing member is between the reservoir and the access member, wherein, when the valve member is inserted into the access member, the valve member extends from the connection portion of the access member to the second opening of the access member.

11. The vial assembly of claim 10, wherein when the cap assembly is fixed to the reservoir:
a planar portion of the first section of the access member is between the housing and the sealing member.

12. The vial assembly of claim 11, wherein the housing is a bendable and hollow cylinder, and wherein ends of the housing are bent toward a center of the hollow cylinder to secure the access member and the sealing member to the reservoir.

13. The vial assembly of claim 12, wherein the housing includes metal.

14. The vial assembly of claim 10, wherein the valve member is a flexible material.

15. The vial assembly of claim 14, wherein the valve member is compressible and includes a top portion with a slit located in the first opening of the connection portion when the valve member is inserted into the access member.

16. The vial assembly of claim 15, wherein the slit, in an uncompressed state of the valve member, seals the contents of the vial at the first opening when the connection portion is not attached to the extraction device, and wherein the slit, in a compressed state of the valve member, provides the access to the contents of the vial when the connection portion is attached the extraction device.

17. The vial assembly of claim 10, wherein the first section and the second section are detachably connected.

18. The vial assembly of claim 10, wherein the connection portion protrudes from a planar portion of the first section and includes a male thread to engage with a female thread of the extraction device.

19. A package, comprising:
a reservoir to hold contents;
an extraction device to extract the contents; and
a cap assembly fixable to the reservoir, the cap assembly including,
an access member including a first section and a second section, the first section including a connection portion that is attachable to the extraction device that extracts contents of the reservoir, the connection portion including a first opening, the second section including a second opening in fluid communication with the contents of the reservoir when the access member is secured to the reservoir,
a valve member insertable into the access member so as to be in fluid communication with the first opening and the second opening and such that the valve member i) seals the contents of the reservoir at the first opening when the connection portion is not attached the extraction device, and ii) provides access to the contents of the reservoir through the first opening when the connection portion is attached to the extraction device, a sealing member, and a housing separate from the reservoir and configured to secure the access member and the sealing member to the reservoir such that the sealing member is between the reservoir and the access member, wherein, when the valve member is inserted into the access member, the valve member extends from the connection portion of the access member to the second opening of the access member.

20. The package of claim 19, wherein the first section of the access member includes a planar portion, and wherein, when the cap assembly is fixed to the reservoir, the housing contacts the planar portion.

* * * * *